United States Patent
Hong et al.

(10) Patent No.: US 9,039,762 B2
(45) Date of Patent: May 26, 2015

(54) ACCOMMODATING INTRAOCULAR LENS USING TRAPEZOIDAL PHASE SHIFT

(75) Inventors: Xin Hong, Fort Worth, TX (US); Mutlu Karakelle, Fort Worth, TX (US); Son Tran, Arlington, TX (US); Xiaoxiao Zhang, Fort Worth, TX (US); Myoung-Taek Choi, Arlington, TX (US)

(73) Assignee: Novartis AG, Basel (CH)

( * ) Notice: Subject to any disclaimer, the term of this patent is extended or adjusted under 35 U.S.C. 154(b) by 176 days.

(21) Appl. No.: 13/042,688

(22) Filed: Mar. 8, 2011

(65) Prior Publication Data

US 2011/0238174 A1     Sep. 29, 2011

Related U.S. Application Data

(60) Provisional application No. 61/316,735, filed on Mar. 23, 2010.

(51) Int. Cl.
  *A61F 2/16*     (2006.01)

(52) U.S. Cl.
  CPC ............ *A61F 2/1629* (2013.01); *A61F 2/1648* (2013.01); *A61F 2002/1683* (2013.01)

(58) Field of Classification Search
  USPC ............ 623/6.27–6.3, 6.32, 6.34, 6.37–6.42, 623/6.46
  See application file for complete search history.

(56) References Cited

U.S. PATENT DOCUMENTS

| | | | | |
|---|---|---|---|---|
| 4,409,690 A | * | 10/1983 | Gess | 623/6.43 |
| 4,434,515 A | * | 3/1984 | Poler | 623/6.41 |
| 5,121,980 A | * | 6/1992 | Cohen | 351/159.41 |
| 5,139,325 A | * | 8/1992 | Oksman et al. | 351/159.02 |
| 5,522,891 A | * | 6/1996 | Klaas | 623/6.37 |
| 5,716,403 A | * | 2/1998 | Tran et al. | 623/6.46 |
| 5,864,378 A | * | 1/1999 | Portney | 351/159.02 |
| 6,179,870 B1 | * | 1/2001 | Sourdille et al. | 623/6.39 |
| 6,228,115 B1 | * | 5/2001 | Hoffmann et al. | 623/6.49 |
| 6,270,220 B1 | * | 8/2001 | Keren | 351/159.42 |
| 6,536,899 B1 | * | 3/2003 | Fiala | 351/159.44 |
| 6,551,354 B1 | * | 4/2003 | Ghazizadeh et al. | 623/6.43 |
| 2002/0068971 A1 | * | 6/2002 | Cumming | 623/6.37 |
| 2002/0072795 A1 | * | 6/2002 | Green | 623/6.34 |

(Continued)

FOREIGN PATENT DOCUMENTS

CN     101277659     12/2010

OTHER PUBLICATIONS

Mawet et al, "Fresnel rhombs as achromatic phase shifters for infrared nulling interferometry", Opt Express, 15(20), (Oct. 2007).*

(Continued)

*Primary Examiner* — Paul Prebilic
(74) *Attorney, Agent, or Firm* — Haynes & Boone, LLP

(57) ABSTRACT

An accommodating intraocular lens (AIOL) includes an optic adapted to produce a trapezoidal phase shift and a plurality of haptics. Each haptic extends from a haptic-optic junction to at least one transverse arm contacting a capsular bag of the eye, and each haptic has sufficient length and rigidity to stretch a capsular bag of the eye to contact ciliary muscles of the eye. The haptic-optic junctions vault the optic forward relative to the haptics and compression of the haptics by the ciliary muscles moves the anterior optic forward. A combined accommodative power produced by the motion of the anterior optic and the trapezoidal phase shift is at least 0.5 Diopters.

15 Claims, 3 Drawing Sheets

(56) References Cited

U.S. PATENT DOCUMENTS

| | | |
|---|---|---|
| 2003/0135272 A1* | 7/2003 | Brady et al. .................. 623/6.37 |
| 2004/0148023 A1* | 7/2004 | Shu .............................. 623/6.34 |
| 2004/0162612 A1* | 8/2004 | Portney et al. ............... 623/6.34 |
| 2006/0230702 A1* | 10/2006 | Doerner ......................... 52/605 |
| 2007/0260308 A1* | 11/2007 | Tran ............................. 623/6.34 |
| 2007/0260310 A1 | 11/2007 | Richardson |
| 2008/0051886 A1* | 2/2008 | Lin ............................... 623/6.34 |
| 2008/0167715 A1* | 7/2008 | Brady et al. .................. 623/6.32 |
| 2008/0243247 A1* | 10/2008 | Poley et al. .................. 623/6.27 |
| 2009/0043384 A1* | 2/2009 | Niwa et al. ................... 623/6.13 |
| 2010/0016965 A1 | 1/2010 | Hong et al. |
| 2010/0204788 A1* | 8/2010 | Van Noy ...................... 623/6.37 |

OTHER PUBLICATIONS

English translation of Chinese Office Action issued for CN201180015437.7 dated Aug. 4, 2014, 13 pgs.

English explaination of Japanese Office Action issued for JP2013-501290 dated Dec. 16, 2014, 8 pgs.

* cited by examiner

ACCOMMODATING INTRAOCULAR LENS USING TRAPEZOIDAL PHASE SHIFT

RELATED APPLICATIONS

This application claims priority to U.S. provisional application Ser. No. 61/316735, filed on Mar. 23, 2010, the contents which are incorporated herein by reference.

TECHNICAL FIELD OF THE INVENTION

The present invention relates intraocular lenses and more particularly to an accommodating intraocular lens (IOL) using a trapezoidal phase shift.

BACKGROUND OF THE INVENTION

The optical power of the eye is determined by the optical power of the cornea and that of the crystalline lens, with the lens providing about a third of the eye's total optical power. The lens is a transparent, biconvex structure whose curvature can be changed by ciliary muscles for adjusting its optical power so as to allow the eye to focus on objects at varying distances. This process is known as accommodation. As a result of accommodation, spherical aberration exhibited by the natural lens shifts in the negative direction.

The natural lens, however, becomes less transparent in individuals suffering from cataract, e.g., due to age and/or disease, thus diminishing the amount of light that reaches the retina. A known treatment for cataract involves removing the opacified natural lens and replacing it with an artificial intraocular lens (IOL). Although such IOLs can improve the patient's vision, they can, however, lead to the loss, or at least severe curtailment, of the eye's accommodative ability. In particular, a class of IOLs, commonly referred to as monofocal IOLs, provide a single optical power and hence do not allow accommodation. Another class of IOLs, commonly known as diffractive IOLs, provide primarily two optical powers, typically a far and a near optical power. As such, these IOLs provide only a limited degree of accommodation, commonly known as pseudoaccommodation.

Single-optic accommodative IOLs translate shape changes in the posterior capsule caused contraction and relaxation of the ciliary muscles into forward motion of the lens, thus providing a degree of accommodation. One difficulty facing such lenses is that the elasticity of the capsular bag can diminish as the capsular bag "shrink wraps" the IOL after surgery. Another difficulty is that the changes in shape of the capsular bag are produced by the tension and relaxation of the zonules, so that the mechanical force exerted on the IOL can be slight. The end result is that the degree of motion produced by single-optic accommodative IOLs is ordinarily insufficient to produce sufficient movement to create any perceptible visual change.

Dual-optic accommodative IOLs are also known that utilize the movement of two optical elements relative to one another in response to the movement of the ciliary muscles to provide a degree of continuous accommodation. However, the range of movement of the two optics of such IOLs is typically limited, thus restricting the range of viewing distance over which they provide accommodation. This in turn limits the degree of accommodation that can be provided.

Accordingly, there is a need for enhanced IOLs, and particularly improved accommodative IOLs as well as for methods of correcting vision that utilize them.

SUMMARY OF THE INVENTION

In particular embodiments of the present invention, an accommodating intraocular lens (AIOL) adapted for implantation in a posterior chamber of an eye includes an optic and a plurality of haptics. Each haptic extending from a haptic-optic junction to at least one transverse arm contacting a capsular bag of the eye, and each haptic has sufficient length and rigidity to stretch a capsular bag of the eye to contact ciliary muscles of the eye. The haptic-optic junctions vault the optic forward relative to the haptics, and compression of the haptics by the ciliary muscles exerts a forward force at the optic of at least 1.5 mN.

In various embodiments of the present invention, an accommodating intraocular lens (IOL) system includes an anterior accommodating IOL and a posterior IOL. The anterior IOL has a positive power anterior optic and a plurality of anterior haptics on opposite sides of the optic along a haptic diameter, each having a transverse arm contacting a capsular bag of the eye, and sufficient length and rigidity to stretch a capsular bag of the eye to contact ciliary muscles of the eye. The haptic-optic junctions vault the optic forward relative to the anterior haptics and compression of the anterior haptics by the ciliary muscles moves the anterior optic forward. The posterior IOL has a posterior optic and posterior haptics. The posterior haptics extend in a radial direction generally perpendicular to the haptic diameter. The posterior haptics are compressed when the capsular bag is stretched by the anterior haptics and the compression of the posterior haptics forces the posterior optic forward.

In certain embodiments of the present invention, an accommodating intraocular lens (AIOL) includes an optic adapted to produce a trapezoidal phase shift and a plurality of haptics. Each haptic extends from a haptic-optic junction to at least one transverse arm contacting a capsular bag of the eye, and each haptic has sufficient length and rigidity to stretch a capsular bag of the eye to contact ciliary muscles of the eye. The haptic-optic junctions vault the optic forward relative to the haptics and compression of the haptics by the ciliary muscles moves the anterior optic forward. A combined accommodative power produced by the motion of the anterior optic and the trapezoidal phase shift is at least 0.5 Diopters.

BRIEF DESCRIPTION OF THE FIGURES

A more complete understanding of the present invention and the advantages thereof may be acquired by referring to the following description, taken in conjunction with the accompanying drawings in which like reference numbers indicate like features.

DETAILED DESCRIPTION OF PREFERRED EXEMPLARY EMBODIMENTS

Various embodiments of the disclosure are illustrated in the FIGURES, like numerals being generally used to refer to like and corresponding parts of the various drawings. As used herein, the terms "comprises," "comprising," "includes,"

"including," "has," "having" or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive or.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example", "for instance", "e.g.", "in one embodiment".

Figure 1:
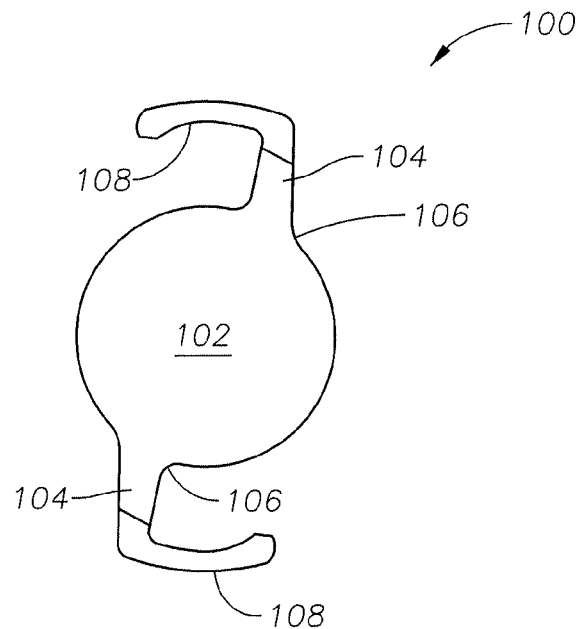
FIG. 1 is an accommodating intraocular lens (AIOL) according to a particular embodiment of the present invention.

FIG. 1 illustrates a single-optic accommodating intraocular lens (AIOL) 100 according to a particular embodiment of the present invention. In general, intraocular lenses (IOLs) as described in this specification are lenses of flexible, transparent, biocompatible materials used to replace the natural lens of the eye, which has been removed for reasons such as the development of cataracts in the natural lens, in order to focus light onto the retina to allow vision. The natural lens is removed using a process such as phacoemulsification, and a generally circular opening, known as a capsulorhexis is typically formed on the anterior side of the capsular bag. The capsulorhexis generally has a diameter of around 5-6 mm, leaving only the outer edge of the anterior side of the capsular bag, sometimes referred to as an anterior "leaflet." The IOL is generally inserted in a folded position through a small incision in the eye into the rhexis, where it is allowed to unfold and is positioned within the capsular bag.

As generally described in this specification, the term "accommodating" refers to moving the optical portion of an IOL forward in response to contraction of the eye's ciliary muscles. The term "forward" or "anterior" as used in this specification refers to the direction generally away from the retina and toward the pupil of the eye, as opposed to "backward" or "posterior." The line normal to the center of the optical portion of the IOL that extends in the forward-backward direction is referred to as the "optical axis." "Radial" refers to any direction extending in a generally perpendicular direction to the optical axis extending through the optical axis, while "lateral" refers to directions perpendicular to the optical axis without necessarily passing through the optical axis.

The AIOL 100 of FIG. 1 includes an optic 102, which is any generally circular, converging optical element capable of producing a focused image on the retina for at least one object distance, and haptics 104. The AIOL 100 is preferably formed as a single piece from a transparent, soft, biocompatible material, such as a cross-linked copolymer of 2-phenyl ethyl acrylate and 2-phenylethyl methacrylate known under the name AcrySof®. The optic 102 may include any suitable form of optical correction, including higher and lower order aberration correction, toric correction, multifocal elements, diffractive elements, or any other optical structure used for visual correction that is known in the art. The haptics 104 each extend from a respective haptic-optic junction 106 to a transverse arm 108 that is generally perpendicular to the extension of the haptic 104 from the optic 102. The transverse arm 108 is configured to contact the capsular bag of an eye when the AIOL 100 is implanted therein. Although only one transverse arm 108 is illustrated in FIG. 1, multiple transverse arms 108 could conceivably be used as well. The distance between the outer edges of the transverse arms 108 of haptics 104 opposite from one another along a diameter of the optic is referred to as the "haptic diameter." In preferred embodiments, the haptic diameter falls with a range from 9.5-11.5 mm, generally corresponding to the range of inner diameter of the ciliary muscles in patients.

A central problem with existing accommodating IOLs, such as those described in U.S. Pat. No. 6,387,126 to Stuart J. Cumming, is the reliance on the transfer of force from the contraction of the ciliary muscles to the IOL by the capsular bag. Since the force from the ciliary muscles is indirectly transferred to the capsular bag by tension of the zonules attached to the bag, this depends heavily on the elasticity of the capsular bag. The difficulty is that the capsular bag drastically changes from its natural shape in the process of "shrink-wrapping" around the IOL, which is much smaller and flatter than the natural crystalline lens. During this process of healing and shrinking, the capsular bag also tends to become less elastic. Furthermore, the natural state of the capsular bag and the surrounding ciliary muscle is circular, but artificial IOLs are typically anisotropic, having a width that is less than the length of the haptics. This makes the post-surgical shape of the capsular bag anisotropic as well and therefore less able to respond to the contraction of the generally circular ciliary muscles and the associated zonule tension. As a result of these changes, after cataract surgery, the ability of the capsular bag to change shape in response to changes in zonular tension is drastically diminished if not eliminated entirely. This sharply limits the effective accommodation response of the IOL to ciliary muscle contraction.

In contrast with existing accommodative IOLs, various embodiments of the present invention provide an AIOL wherein the haptics are configured to stretch the capsular bag to contact the ciliary muscles directly. Thus, contraction of the ciliary muscles directly moves the haptics, rather than being mediated through zonular tension or the elasticity of the capsular bag. Likewise, the haptics are specially designed with forward vaulting to move the optic forward in response to the contraction. Finally, the haptics have transverse arms that contact the capsular bag, so that the portion of the haptics extending from the optic to the capsular bag can be of sufficiently small width to easily bend in response to forces from the capsular bag while still being sufficiently rigid to stretch the capsular bag. This may be contrasted with plate haptics of previous systems that would require excessive force from the ciliary muscles to move and, conversely, would be prone to cause damage to the ciliary tissue, including necrosis. The Young's modulus of the material can also be suitably selected with the size and angulation of the haptics 104 to have the desired mechanical properties enabling adequate forward movement of the optic 102; preferably, the Young's modulus is between 0.8 and 3 mPa. In particular, the force exerted on the optic 102 by the haptics 104 under compression should be sufficient to overcome the resistance of the anterior capsular leaflet, which will have "shrink-wrapped" onto the haptics 104. This can vary somewhat based on the size of the anterior capsulorhexis in which the AIOL 100 is implanted, but based on mechanical simulations and clinical investigation, a force of 1.5 mN appears to be sufficient at least for the majority of patients.

Figure 2:
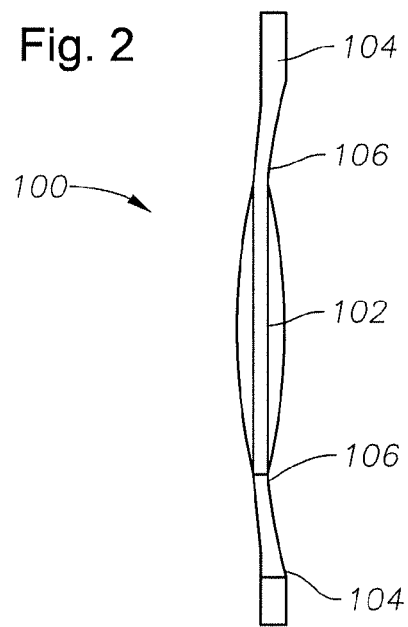
FIG. 2 is a side view of the AIOL of FIG. 1.

FIG. 2 is a side view of the AIOL 100 of FIG. 1 illustrating particular adaptations of the AIOL 100 to provide better forward motion of the IOL. The haptic-optic junctions 106 are angled to vault the optic 102 forward of the haptics 104 to facilitate forward movement. In particular, the depicted embodiment shows a forward vault angle of 10 degrees for the haptic-optic junction 106, while the haptic-optic junction is also made thinner relative to the haptics 104 so that the anterior angle of intersection with the optic is 175 degrees. Preferably, the forward vault angle is at least 5 degrees. In the depicted embodiment, the thicknesses of the haptics 104 (referring to the thickness in the anterior-to-posterior direction) are 0.45 mm, and the haptic-optic junction 106 gradually narrows in thickness according to the described angles to match the edge thickness of the optic 102 (0.25 mm).

Figure 3:
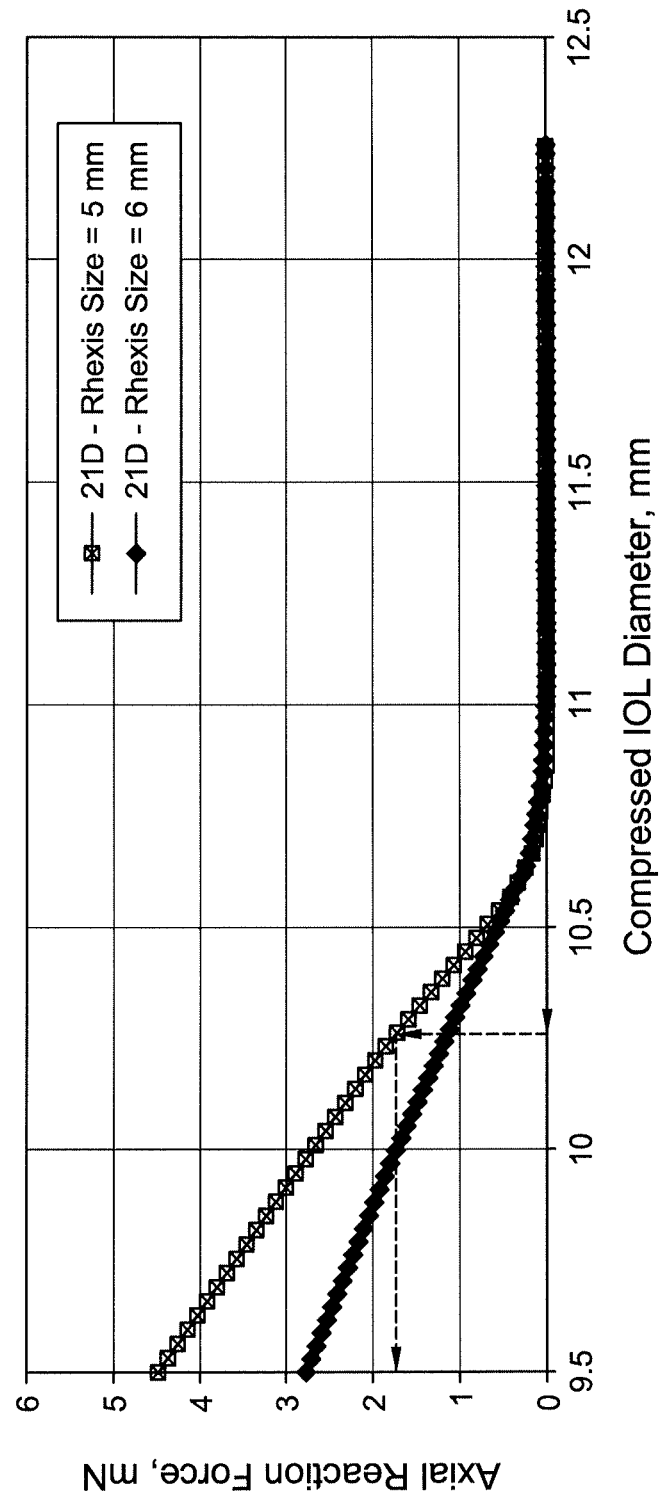
FIG. 3 is a graph of simulated axial reaction force versus ciliary muscle diameter for an AIOL according to a particular embodiment of the present invention.

FIG. 3 is a graph showing simulated force on the optic 102 that would be exerted by contraction of the ciliary muscles to a certain diameter. In the example shown in FIG. 3, an AIOL 100 like the one depicted in FIGS. 1 and 2 has a haptic diameter of 10.8 mm, corresponding to the average inner diameter of the ciliary muscles. The simulated AIOL 100 is formed from the AcrySof® material. As shown in the graph, the force exerted on the optic 102 by the compression of the ciliary muscles exceeds 1.5 mN for a normal degree of ciliary muscle contraction (around 0.3 mm). In the example AIOL 100, this is sufficient to produce about 0.5 mm of displacement along the optical axis, corresponding to an effective accommodative power change around 0.7 Diopters.

Figure 4:
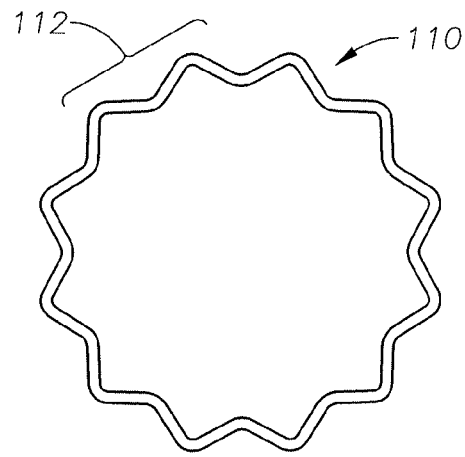
FIG. 4 is a capsular ring for use with an AIOL according to a particular embodiment of the present invention.

As noted above, there can be considerable variations in the inner diameter of the ciliary muscles. Although the haptics 104 will be sized to fit within specific diameters, the fit may not be perfect. For that reason, capsular rings used to help fit the haptics 104 securely within the capsular bag may also be used in conjunction with various embodiments of the present invention to improve the fit within the inner diameter of the ciliary muscles once the capsular bag is stretched. FIG. 4 illustrates a flexible capsular ring 110 useful with various embodiments of AIOLs such as AIOL 100. The capsular ring 110 is formed from a flexible, biocompatible material and includes collapsible portions 112 that can fold and unfold to fit the capsular ring 110 within a certain diameter. Similarly, when the haptics 104 of the AIOL 100 stretch the capsular bag, the capsular ring 110 can suitably change shape as well. It should be understood that various embodiments of the present invention can be used in conjunction with capsular rings such as the capsular ring 110 depicted in FIG. 1. When there is reference herein to "contact" with the capsular bag or the ciliary muscles, this can refer either to direct contact of the element with the structure in question or to mediated contact with the structure by way of the capsular ring 110. Thus, the term "contact" should be suitably interpreted to encompass both meanings.

While the described mechanical configuration produces some degree of accommodative response, the power change alone is still somewhat small, so that it might not have a major effect on functional vision. What can make the impact of the motion even more significant is the use of optical designs that augment the visual effects of the motion. For that reason, it is advantageous to incorporate into the optical design certain optical features providing improved depth of focus that will change based on the forward motion of the optic 102. One such optical feature is the trapezoidal phase shift, described in U.S. Pat. No. 8,241,354, entitled "AN EXTENDED DEPTH OF FOCUS (EDOF) LENS TO INCREASE PSEUDO-ACCOMMODATION BY UTILIZING PUPIL DYNAMICS" which is commonly assigned to the owner of the present application and which is incorporated herein by reference. As described in that patent, a linear change in the phase shift imparted to incoming light as a function of radius (referred to herein as a "trapezoidal phase shift") can adjust the effective depth of focus of the IOL for different distances and pupil sizes. In this manner, the trapezoidal phase shift provides different apparent depth of focus depending on pupil size, allowing the image to change as a result of changes in light conditions. This in turn provides slightly different images for conditions in which one would be more likely to be relying on near or distance vision, allowing the patient's visual function to better operate under these conditions, a phenomenon known as "pseudo-accommodation." But in the context of an AIOL similar to the one shown in FIG. 1, the trapezoidal phase shift also changes as the optic 102 moves forward. This effectively combines the pseudo-accommodative effect for near and far vision with the actual shift in power toward near vision, thus augmenting the visual effects of the forward motion and improving the degree of performance. In terms of effective visual performance, this can allow a combined effective power change of 0.75 Diopters or more.

Figure 5:
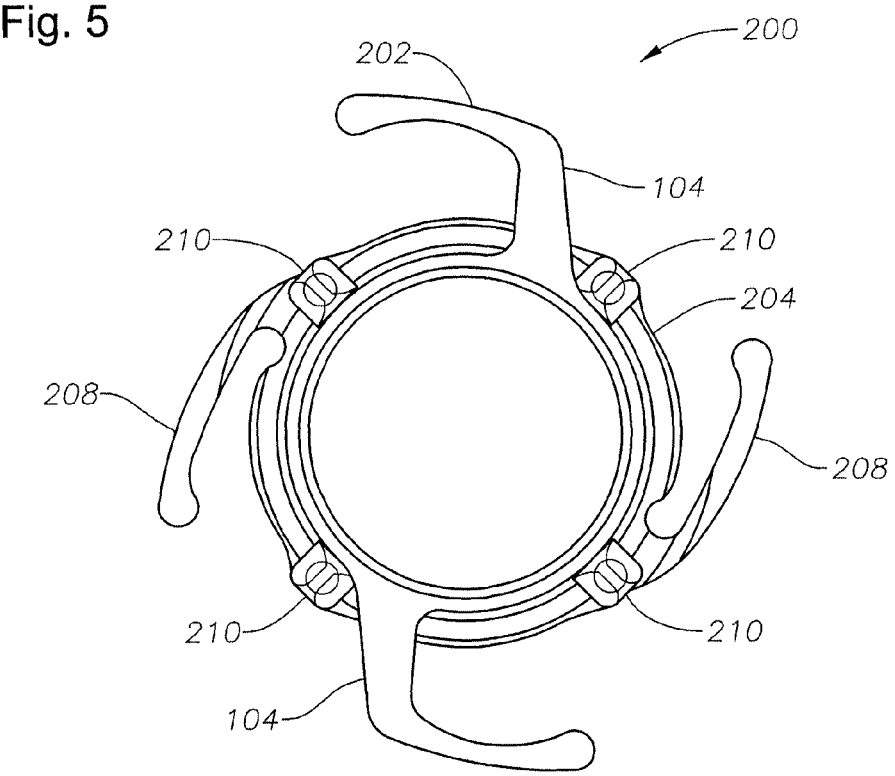
FIG. 5 is a dual-optic accommodating IOL system according to a particular embodiment of the present invention.
Figure 6:
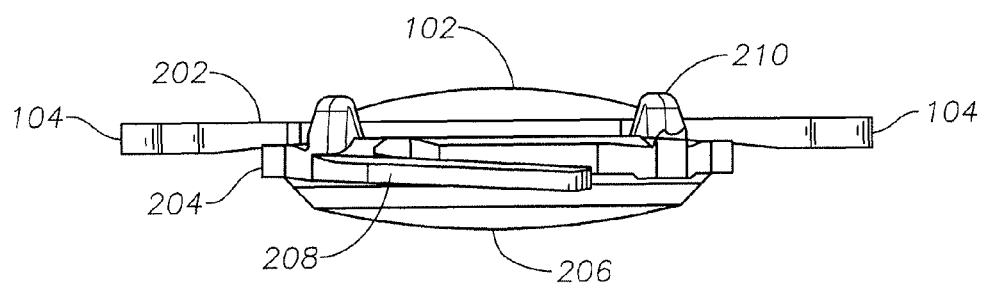
FIG. 6 is a top view of the dual-optic accommodating IOL system of FIG. 5.

The previously described embodiments involve a single-lens, single optic AIOL 100. However, the various embodiments of the present invention are not limited to single-optic AIOLs. FIG. 5 depicts a dual-lens, dual-optic AIOL system 200 according to a particular embodiment of the present invention. In the depicted embodiment, the anterior IOL 202 is an accommodating IOL such as the AIOL 100 depicted in FIG. 1. Any of the foregoing description of the embodiments and features of AIOL 100 is equally applicable to the anterior IOL 202. The AIOL system 200 further includes a posterior IOL 204. The posterior IOL 204 also includes an optic 206 and haptics 208. The posterior IOL 204 is also preferably formed as a single piece from a flexible, transparent, biocompatible material, which may include cross-linked copolymer of 2-phenyl ethyl acrylate and 2-phenylethyl methacrylate known under the name AcrySof®.

Although both the anterior IOL 202 and the posterior IOL 204 could in principle be converging lenses, it is particularly advantageous for the posterior IOL 204 to have a negative power optic 208. This allows aberrations of the IOLs 202 and 204 to offset one another and also magnifies the degree that the power increases when the IOLs 202 and 204 are separated by a certain distance. Further, like the optic 102 of the anterior IOL 202, the optic 206 of the posterior IOL 204 may include any suitable form of optical correction, including higher and lower order aberration correction, toric correction, multifocal elements, diffractive elements, or any other optical structure used for visual correction that is known in the art, and the optics 102 and 206 may be suitably designed to work in combination to produce such results. In particular, the aforementioned trapezoidal phase shift can be used to considerable advantage in the IOL system 200 of FIG. 5 as well.

The posterior IOL 204 also includes novel mechanical features designed to reduce the amount of separation between the IOLs 202 and 204 when the ciliary muscles are relaxed. This advantageously allows greater separation of the IOLs 202 and 204 within the space of the capsular bag when the ciliary muscles are contracted, thus increasing the effective accommodation of the IOL system 200. In particular, the haptics 208 extend in a direction generally perpendicular to the haptic diameter of the anterior IOL 202. The haptics 208 are designed to push the posterior IOL 204 forward when the capsular bag is fully stretched by the haptics 104 of the anterior IOL 202, thus drawing the sides of capsular bag inward and compressing the haptics 208 of the posterior IOL 204. This is in marked contrast to previous dual-optic designs, which emphasized the motion of the higher-power anterior lens, taking the posterior lens as having an essentially fixed position against the posterior wall of the capsular bag. Unlike these previous dual-optic IOL systems, the haptics 208 of the posterior IOL 204 in the embodiment depicted in FIG. 5 actually force the posterior optic 208 away from the posterior wall of the capsular bag, putting the anterior IOL 202 and the posterior IOL 204 in closer proximity in the rest position.

The posterior IOL 204 depicted in FIG. 5 also includes protrusions 210 placed around the anterior surface of the posterior IOL 204. The protrusions 210 push against the anterior leaflet of the capsular bag to reduce the amount of force exerted against the anterior IOL 202, thus allowing the anterior IOL 202 to move more easily. The protrusions 210 also prevent the anterior leaflet from exerting force on the anterior IOL 202 and posterior IOL 204 when the ciliary muscles are relaxed, which helps to maintain the ability of the anterior IOL 202 and the posterior IOL 204 to separate from one another when the ciliary muscles contract and the tension in the capsular bag is reduced. Lastly, the protrusions 210 can provide a rotational alignment guide for the anterior IOL 202, and suitable markings can also be placed relative to the protrusions 210 to further facilitate alignment. Thus, after the posterior IOL 204 is placed, the anterior IOL 202 can then be accordingly placed by a surgeon relative to the protrusions 210. The protrusions 210 would also restrict any rotational motion of the anterior IOL 202. These features can be particularly advantageous when the optic 102 of the anterior IOL 202 includes toric correction, which is sensitive to the rotational alignment of the anterior IOL 202.

Although embodiments have been described in detail herein, it should be understood that the description is by way of example only and is not to be construed in a limiting sense. For example, while a particular example of a testing method has been presented, it should be understood that the testing method could also be modified in a manner consistent with any of the various test selection methods and image parameter variations described herein. It is to be further understood, therefore, that numerous changes in the details of the embodiments and additional embodiments will be apparent to, and may be made by, persons of ordinary skill in the art having reference to this description. It is contemplated that all such changes and additional embodiments are within scope of the claims below and their legal equivalents.

What is claimed is:

1. An accommodating intraocular lens (AIOL) adapted for implantation in a posterior chamber of an eye, comprising:
   an optic comprising two optical regions having an identical optical power and adapted to produce a trapezoidal phase shift, the trapezoidal phase shift being a linear change between the two regions in the phase shift imparted to incoming light as a function of radius;
   a plurality of haptics, each haptic extending from a haptic-optic junction to at least one transverse arm adapted for contacting a capsular bag of the eye and each haptic having sufficient length and rigidity to stretch a capsular bag of the eye to contact ciliary muscles of the eye;
   wherein the haptic-optic junctions vault the optic forward relative to the haptics and compression of the haptics by the ciliary muscles exerts a forward force at the optic of at least 1.5 mN, wherein the trapezoidal phase shift augments the visual effect of the forward force to produce a combined effective power change of at least 0.75 Diopters.

2. The AIOL of claim 1, wherein at least two of the haptics extend along a diameter of the optic and a distance between the transverse arms of the haptics along the diameter is between 9.5 and 11.5 mm.

3. The AIOL of claim 2, wherein the distance between the transverse arms along the diameter is at least 10 mm.

4. The AIOL of claim 1, wherein a vault angle of the haptic-optic junctions is at least 5 degrees.

5. The AIOL of claim 1, wherein the forward force at the optic is at least 1.5 mN when the haptics are compressed inwardly by 0.5 mm.

6. The AIOL of claim 1, wherein the transverse arms of the haptics extend from a square elbow.

7. The AIOL of claim 1, wherein the AIOL is a single-piece AIOL formed from a material having a Young's modulus of 0.8 to 3 mPa.

8. The AIOL of claim 1, further comprising a capsular ring around the haptics, the capsular ring having collapsible sections allowing the capsular ring to conform to the capsular bag as the capsular bag is stretched by the haptics.

9. An accommodating intraocular lens (IOL) system, comprising:
   an anterior accommodating IOL comprising a positive power anterior optic comprising two optical regions having an identical optical power and adapted to produce a trapezoidal phase shift, the trapezoidal phase shift being a linear change between the two regions in the phase shift imparted to incoming light as a function of radius, and a plurality of anterior haptics on opposite sides of the optic along a haptic diameter, each anterior haptic extending along the haptic diameter from a haptic-optic junction to at least one transverse arm adapted for contacting a capsular bag of the eye and each anterior haptic having sufficient length and rigidity to stretch a capsular bag of the eye to contact ciliary muscles of the eye, wherein the haptic-optic junctions vault the optic forward at a vault angle relative to the anterior haptics and compression of the anterior haptics by the ciliary muscles moves the anterior optic forward, wherein the trapezoidal phase shift augments the visual effect of forward motion of the positive power anterior optic to produce a combined effective power change of at least 0.75 Diopters; and
   a posterior IOL comprising a posterior optic and posterior haptics, the posterior haptics extending in a radial direction perpendicular to the haptic diameter, wherein the posterior haptics are compressed when the capsular bag is stretched by the anterior haptics and the compression of the posterior haptics forces the posterior optic forward.

10. The accommodating IOL system of claim 9, wherein the posterior optic is a negative power optic.

11. The accommodating IOL system of claim 9, wherein the posterior IOL further comprises a plurality of protrusions around an anterior surface of the posterior IOL, the protrusions extending to an anterior side of the capsular bag.

12. The accommodating IOL system of claim 9, wherein the vault angle of the haptic-optic junctions is at least 5 degrees.

13. An accommodating intraocular lens (AIOL) comprising:
   an optic comprising two optical regions having an identical optical power and adapted to produce a trapezoidal phase shift, the trapezoidal phase shift being a linear change between the two regions in the phase shift imparted to incoming light as a function of radius; and
   a plurality of haptics, each haptic extending from a haptic-optic junction to a square elbow with a single transverse arm adapted for contacting a capsular bag of the eye extending from the square elbow and each haptic having sufficient length and rigidity to stretch a capsular bag of the eye to contact ciliary muscles of the eye, wherein the haptic-optic junctions vault the optic forward relative to the haptics and compression of the haptics by the ciliary muscles moves the optic forward, and wherein a combined accommodative power produced by the motion of the anterior optic and the trapezoidal phase shift is at least 0.5 Diopters.

14. The AIOL of claim 13, wherein the combined accommodative power is at least 1.0 Diopters.

15. The AIOL of claim 13, wherein the optic moves forward at least 0.3 mm when the haptics are compressed by the ciliary muscles.

* * * * *